US008524459B2

(12) United States Patent
Giuliani et al.

(10) Patent No.: US 8,524,459 B2
(45) Date of Patent: *Sep. 3, 2013

(54) METHOD FOR THE IN VITRO DIAGNOSIS OF STROKE

(75) Inventors: Isabelle Giuliani, Garches (FR); Catherine Larue, Vaucresson (FR); Johann Guegan, Rueil Malmaison (FR)

(73) Assignee: Bio-Rad Innovations, Marnes-la-coquette (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/056,432

(22) PCT Filed: Jul. 31, 2009

(86) PCT No.: PCT/EP2009/059982
§ 371 (c)(1),
(2), (4) Date: Mar. 7, 2011

(87) PCT Pub. No.: WO2010/012834
PCT Pub. Date: Feb. 4, 2010

(65) Prior Publication Data
US 2011/0312517 A1    Dec. 22, 2011

(30) Foreign Application Priority Data

Aug. 1, 2008 (WO) ................. PCT/EP2008/060188
Jan. 30, 2009 (WO) ................. PCT/EP2009/051101

(51) Int. Cl.
*G01N 33/53* (2006.01)

(52) U.S. Cl.
USPC ............................................ 435/7.1; 436/518

(58) Field of Classification Search
None
See application file for complete search history.

(56) References Cited

FOREIGN PATENT DOCUMENTS

| WO | 2004/014952 A2 | 2/2004 |
| WO | 2006/088700 | 8/2006 |

OTHER PUBLICATIONS

International Search Report received in related PCT/EP2009/059982; Nov. 16, 2009.
Seferian et al. "The Brain Natriuretic Peptide (BNP) Precursor is the Major Immunoreative Form of BNP in Patients with Heart Failure"; US American Association for Clinical Chemistry; vol. 53, No. 5; May 2007.

*Primary Examiner* — Jacob Cheu
(74) *Attorney, Agent, or Firm* — ALG Intellectual Property, LLC (57) ABSTRACT

The present invention relates to a method for the in vitro diagnosis of stroke and transient ischemic attack (TIA) in an individual, comprising the following steps:
(a) measuring the level of proBNP(1-108), or of fragments of proBNP(1-108) comprising a RAPRSP sequence (SEQ ID NO: 1), in a biological sample of the individual;
(b) comparing the measured level with a cut-off value;
(c) determining therefrom whether a stroke or a TIA has occurred in the individual.

21 Claims, 6 Drawing Sheets

METHOD FOR THE IN VITRO DIAGNOSIS OF STROKE

FIELD OF THE INVENTION

The present invention relates to methods and kits for the in vitro diagnosis of stroke.

BACKGROUND OF THE INVENTION

Stroke, also known as cerebrovascular accident (CVA), is one of the leading causes of mortality and morbidity with an estimated 700,000 patients diagnosed with stroke each year. Stroke currently ranks third in the cause of death in the U.S.A.

The term "stroke" encompasses two widely different clinical settings which it is of the utmost importance to distinguish. Ischemic stroke is thus usually caused by the blockage of blood vessels and is best treated by clot dissolving agents, such as t-PA, within three hours of symptom onset. In contrast, hemorrhagic stroke is caused by bleeding into the brain which forbids any treatment by anti-clotting agents, which could prove fatal.

Transient ischemic attack (TIA, often colloquially referred to as "mini stroke") is caused by the changes in the blood supply to a particular area of the brain, resulting in brief neurologic dysfunction that persists, by definition, for less than 24 hours; if symptoms persist then it is categorized as a stroke (see e.g. Transient Ischemic Attacks: Stroke (CVA): Merck Manual Home Edition). Patients diagnosed with a TIA are sometimes said to have had a warning for an approaching stroke. If the time period of blood supply impairment lasts more than a few minutes, the nerve cells of that area of the brain die and cause permanent neurologic deficit. One third of the people with TIA later have recurrent TIAs and one third have a stroke due to permanent nerve cell loss (Transient ischemic attack Mount Sinai Hospital, New York). Therefore, the identification of TIA is beneficial because these patients are at increased risk of future stroke.

The diagnosis of stroke, and the segmentation between ischemic and hemorrhagic stroke, in patients which present with symptoms indicative of stroke, such as sudden numbness or blindness, confusion, severe headaches, slurred speech, and partial paralysis, currently essentially relies on computed tomography (CT). CT, however, is not completely satisfying since it has an estimated sensitivity of less than 26% in diagnosing acute stroke (Chalela et al. (2007) Lancet 369:293-298), which is linked to a very poor performance in detecting ischemic stroke, with less than 33% sensitivity (Reynolds et al. (2003) Clin. Chem. 49:1733-1739). Magnetic resonance imaging (MRI) has been shown to be superior to CT in diagnosing acute stroke (84% sensitivity, Chalela et al. (2007) Lancet 369:293-298), and particularly ischemic stroke. However MRI scanners are costly equipments and are not always available in the emergency room.

Accordingly there is still the need for alternative or complementary methods, in particular to CT, for diagnosing stroke and TIA.

In this respect, biochemical markers have been suggested as an aid in detecting stroke, in particular in view of the early detection of ischemic stroke.

S-100b (a marker of astrocytic activation) and neuron-specific enolase (NSE) are among the best characterized such markers (Jauch et al. (2006) Stroke 37:2508-2513). Heart-type fatty acid binding protein(H-FABP) has also been considered as a promising marker (Lescuyer et al. (2005) Mol. Diagn. 9:1-7). However, it seems that the discriminatory power offered by these markers individually is not sufficient to be of clinical value.

It has thus been suggested to use panels combining several markers, such as S-100b, the B-type neurotrophic growth factor (BNGF), the von Willebrand factor (vWF), matrix metalloproteinase-9 (MMP-9) and monocyte chemotactic protein-1 (MCP-1), for diagnosing ischemic stroke (Reynolds et al. (2003) Clin. Chem. 49:1733-1739). Indeed, this panel was shown to provide a sensitivity of 92% at 93% specificity for ischemic stroke sample within 6 hours from symptom onset. Within 3 hours from onset however, sensitivity is of only 87%, which might be due to a too low individual sensitivity/specificity of the markers.

Accordingly, there is still the need for alternative markers offering a good individual sensitivity/specificity ratio to be used in single-marker tests or to improve multi-marker panels, either by increasing sensitivity/specificity or by enabling reducing the number of markers which levels have to be measured in panels.

proBNP(1-108), a precursor protein of 108 amino acids, is cleaved in vivo to yield (i) Brain Natriuretic Peptide (also referred to as BNP(32) or simply BNP), which consists of the 32 C-terminal amino acids of proBNP(1-108) and (ii) NT-proBNP(1-76), which consists of the 76 N-terminal amino acids of proBNP(1-108) (Giuliani et al. (2006) Clinical Chemistry 52:1054-61). Biologically, BNP is a blood pressure regulatory agent which is released mainly from the left cardiac ventricle in response to volume expansion and pressure overload. proBNP(1-108) has been shown to be circulating in patients with severe heart failure (Hammerer-Lercher et al. (2008) Clinical Chemistry 54:5).

SUMMARY OF THE INVENTION

The present invention arises from the unexpected finding, by the inventors, that proBNP(1-108) alone had a high discriminatory power (e.g. 95% sensitivity and 95% specificity as measured in plasma samples) in stroke detection.

Thus, the present invention relates to a method for the in vitro diagnosis of stroke and Transient ischemic attack (TIA) in an individual, comprising the following steps:

(a) measuring the level of proBNP(1-108), or of fragments of proBNP(1-108) comprising a RAPRSP sequence (SEQ ID NO: 1), in a biological sample of the individual;

(b) comparing the measured level with a cut-off value;

(c) determining therefrom whether a stroke or a TIA has occurred in the individual.

In an embodiment of the above defined method, the invention more particularly relates to a method, comprising the following steps:

(a') measuring the level of proBNP(1-108), or of fragments of proBNP(1-108) comprising a RAPRSP sequence (SEQ ID NO: 1), in a biological sample of the individual;

(b') measuring the level of at least one further stroke marker in a biological sample of the individual;

(c') comparing the level of proBNP(1-108), or of fragments of proBNP(1-108), and the level of the at least one further stroke marker, with one or several cut-off values;

(d') determining therefrom whether a stroke or a TIA has occurred in the individual.

In another embodiment of the invention, the above-defined method further comprises measuring the level of at least one marker of cardiovascular diseases.

The present invention also relates to a kit for diagnosing stroke, comprising:

at least one antibody suitable for detecting proBNP(1-108), or fragments of proBNP(1-108) which comprise a RAPRSP sequence (SEQ ID NO: 1); and at least one calibrator comprising proBNP(1-108), or a fragment of proBNP(1-108) which comprise a RAPRSP sequence (SEQ ID NO: 1), preferably at a concentration of 1 to 1000 pg/ml.

The present invention also relates to the use of proBNP(1-108), or of fragments of proBNP(1-108) which comprise a RAPRSP sequence (SEQ ID NO: 1), for the in vitro diagnosis of stroke or TIA.

DETAILED DESCRIPTION OF THE INVENTION

As intended herein "diagnosing" or establishing a "diagnosis" relates to determining if a stroke has occurred in an individual.

As intended herein "stroke" relates to all cerebrovascular accidents. In particular, the term "stroke" encompasses acute and chronic stroke as well as ischemic and hemorrhagic stroke.

Ischemic stroke is characterized by a partial or total occlusion of cerebral vessels which may lead to infarction and necrosis of cerebral tissues supplied by these vessels. In transient ischemic attack (TIA) the occlusion ceases spontaneously causing a dysfunction which lasts for no more than 24 hours.

Hemorrhagic stroke is characterized by an intracerebral haemorrhage generally from cerebral vessel rupture.

Preferably, the stroke according to the invention is selected from the group consisting of an ischemic stroke and a hemorrhagic stroke. More preferably, the stroke as intended herein is acute ischemic stroke.

Advantageously, the method of the invention provides for early stroke diagnosis. Early stroke diagnosis is of particular importance in the case of ischemic stroke, since it is usually estimated that treating the occluded vessels within 3 hours of stroke symptoms onset will prevent most irreversible cerebral damages. Accordingly, it is preferred that the above defined step (a) is implemented within 6 hours, more preferably within 3 hours, and most preferably within 2 hours, after the onset of at least one symptom indicative of stroke in the individual.

The symptoms indicative of stroke are well known to one of skill in the art and notably encompass sudden numbness or blindness, confusion, severe headaches, slurred speech, and partial paralysis.

The individual is preferably a human.

"proBNP(1-108)" relates to the precursor BNP(32) and of NT-proBNP(1-76). As intended herein "proBNP(1-108)" encompasses all its natural variants. By way of example proBNP(1-108) is represented by SEQ ID NO: 4.

In vivo, proBNP(1-108) is often partially truncated, in particular it is deleted of one or more amino acids on the N-terminal side or optionally on the C-terminal side, for instance by circulating proteases, to form so-called "proBNP (1-108) fragments". An example of such a proBNP(1-108) fragment, the proBNP(3-108) fragment produced by cleavage by a dipeptidase, is described in Lam et al. (2007) J. Am. Coll. Cardiol. 49:1193-1202. It is believed that it is not only proBNP(1-108) which is of diagnosis value but also its various natural fragments. Accordingly, the present invention not only relies on measuring the level of proBNP(1-108) but also the level of fragments of proBNP(1-108).

The expression "proBNP(1-108)" and "fragments of proBNP(1-108)" also include any polypeptide having been subjected to at least one post-translational modification, such as phosphorylation, glycosylation or the like. For example, Schellenberger et al. (2006) Arch. Biochem. Biophys. 51:160-6 have shown that proBNP(1-108) is a glycoprotein which is O-glycosylated either entirely or in part.

As intended herein the fragments of proBNP(1-108) comprise the RAPRSP sequence (SEQ ID NO: 1). This RAPRSP sequence harbours the site of proBNP(1-108) which is cleaved in vivo to yield NT-proBNP(1-76) and BNP(32). As such, the RAPRSP is specific of proBNP(1-108) and cannot be found in BNP(32) nor in NT-proBNP(1-76), which are thus excluded from the definition of the fragments of proBNP (1-108) according to the invention.

It is further preferred that the fragments of proBNP(1-108) according to the invention comprise a FGRKMDR sequence (SEQ ID NO: 2). This sequence is comprised in the BNP(32) part of proBNP(1-108). Even more preferably, the fragments of proBNP(1-108) comprise the whole sequence of BNP(32) (SEQ ID NO: 3).

The expression "further stroke marker" relates to any biochemical marker, other than proBNP(1-108) or fragments of proBNP(1-108) as defined above, which level is indicative of stroke or TIA as defined above.

The expression "marker of cardiovascular diseases" relates to any marker useful for detecting or diagnosing a cardiovascular disease. Such markers are well known to one of skill in the art. Preferably, the marker of cardiovascular diseases is selected from the group constituted of the C reactive protein (CRP) and cardiac troponin I (cTnI). Measuring the level of a marker of cardiovascular diseases may be advantageous in the method of the invention since it enables excluding cardiovascular diseases as a cause for variation of the level of proBNP (1-108).

Preferably, measuring or determining the level of proBNP (1-108), of fragments of proBNP(1-108), of the at least one further stroke marker, or of the at least one marker of cardiovascular diseases, is determined using an immunoassay.

As intended herein an "immunoassay" relates to any method wherein the level of proBNP(1-108), of fragments of proBNP(1-108), of the at least one further stroke marker, or the at least one marker of cardiovascular diseases, is determined using at least one compound (or ligand) specifically binding thereto. The compound (or ligand) specifically binding thereto can be of any type but it is preferred that it is an antibody, an aptamer, or a peptide obtained by phage display. Immunoassay methods are well known to one of skill in the art and may be carried out in accordance with various formats well-known to the one skilled in the art, for example in solid or homogeneous phase, in one or two steps, by a sandwich method or by a competitive method.

Preferably, the sandwich method in solid phase between 2 ligands, one being a capture ligand and the other being a detection ligand, will be used. This type of immunoassay is particularly well-known to one skilled in the art. For example, the article by Seferian et al. (2007) *Clin. Chem.* 53:866-873 gives an example of a sandwich immunoassay (or immunometric assay at 2 sites) for assaying BNP(32) and proBNP(1-108), each time using a pair of antibodies (an antibody immobilised in solid phase and an labelled antibody in detection).

The presence of the antigen in the biological sample is revealed by detection means, in particular a "detection ligand". A detection ligand, which is labelled, is able to bind to the captured antigen, by recognising an epitopic site which is different from that recognised by the capture ligand.

The term "labelled" refers both to a direct labelling and to an indirect labelling (for example, by means of other ligands, themselves directly labelled, or using reagents of a labelled "affinity pair", such as, but not exclusively, the labelled avidin-biotin pair, etc.).

In the case of the sandwich method, the capture ligand is preferably selected in such a way that it specifically recognises an epitope on the natural antigen of the patient, whilst the detection ligand is selected preferably in such a way that it specifically recognises another epitope on the natural antigen of the patient.

Preferably, the capture ligand is immobilised on a solid phase. By way of non-limiting examples of solid phase, microplates could be used, in particular polystyrene microplates, such as those sold by Nunc, Denmark. Solid particles or beads, paramagnetic beads, such as those produced by Dynal, Merck-Eurolab (France) (under the trademark Estapor™) and Polymer Laboratories, or even polystyrene or polypropylene test tubes, glass, plastic or silicon chips, etc. may also be used.

ELISA assays, radioimmunoassays, or any other detection method may be used to reveal the presence of formed antigen-antibody complexes. Thus, different types of labelling of ligands in particular of antibodies, are possible (radioactive, ezymatic, fluorescent, etc.).

The detection may also be carried out by methods based on mass accumulation, such as surface plasmon resonance (SPR), by piezo-electric detection, but also by mass spectrometry or any other methods defined as enabling the study of a ligand-antigen-type interaction in the absence of a second labelled ligand.

The term "specific", when it refers to recognition of a ligand or binding of a ligand to a target, means that the ligand interacts with the target without interacting substantially with another target which does not structurally resemble the target.

An "antibody" as intended herein relates to antibodies belonging to any species, such as human, mouse, rat, rabbit, goat, or camelidae species. The antibody can also be a chimeric antibody, i.e. an antibody which comprises parts originating from different species. Preferred chimeric antibodies are so-called "humanized" antibodies, wherein the constant parts ($C_H$ and $C_L$) are of human origin and the variable parts ($V_H$ and $V_L$) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')$_2$, scFv fragments as well as camelidae single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) *Nature* 346:818-22 and Bock et al. (1992) *Nature* 355:564-6. The aptamers of a peptide nature and the production thereof are described, in particular, by Hoppe-Seyler et al. (2000) *J. Mol Med.* 78:426-30.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott & Smith (1990) *Science* 249:386-390, and Marks et al. (1991) *J. Mol. Biol.* 222:581-597. Preferably, the polypeptide obtainable by phage display is an scFv-type polypeptide (single-chain variable fragment). This technique is described, in particular, by Winter et al. (1994) *Annu. Rev. Immunol.* 12:433-455.

Preferably, the above-defined immunoassay comprises an antibody targeting an epitope which comprises the RAPRSP sequence (SEQ ID NO: 1). More preferably, the antibody is secreted by the hybridoma deposited at the CNCM (Collection Nationale de Cultures de Microorganismes, Institut Pasteur, 25, rue du Docteur Roux, 75 724 Paris Cedex 15, France) under the Budapest Treaty on Apr. 29, 2005, under reference number I-3073. Such an antibody is notably described in the international publication WO 2004/014952. This antibody is advantageous, in that it enables the specific detection of proBNP(1-108) and of all the fragments of proBNP(1-108) according to the invention, with the notable exception of BNP(32), NT-proBNP(1-76) and their respective fragments, thereby ensuring obtaining the full diagnosis benefits of proBNP(1-108) and its various fragments.

Preferably also, the immunoassay comprises an antibody targeting an epitope which comprises the FGRKMDR sequence. More preferably, the antibody is secreted by the hybridoma deposited by Bio-Rad (3 boulevard Raymond Poincaré, 92430 Marnes la Coquette, France) at the CNCM (Collection Nationale de Cultures de Microorganismes, Institut Pasteur, 25, rue du Docteur Roux, 75 724 Paris Cedex 15, France) under the Budapest Treaty on Apr. 13, 2007, under reference number I-3746. Such an antibody is notably described in international application PCT/EP2008/060188.

Advantageously, the antibody targeting an epitope which comprises the RAPRSP sequence (SEQ ID NO: 1) and the antibody targeting an epitope which comprises the FGRKMDR sequence are combined in a same immunoassay, thereby enabling the specific detection of proBNP(1-108) or of fragments of proBNP(1-108) according to the invention.

Preferably, where proBNP(1-108), or fragments of proBNP(1-108) are concerned, the cut-off value as defined above is of at least the mean level of proBNP(1-108), or of fragments of proBNP(1-108) according to the invention in biological samples obtained from an apparently healthy population of individuals. More preferably, the above-defined cut-off value is of at least the value corresponding to the 75th percentile, the 95th percentile, or the 99th percentile of the levels of proBNP(1-108), or of fragments of proBNP(1-108) according to the invention obtained from an apparently healthy population of individuals. Most preferably, this cut-off value is of at least 0, 1, 2, 3, 5, 10, 50 or 100 pg/ml. Where the cut-off value is of at least 0 pg/ml this means that the above defined steps a) and b), or a') and c'), of the method of the invention consist simply in determining whether proBNP(1-108), or fragments of proBNP(1-108), as defined above are present in the biological sample of the individual.

Similarly, where the at least further stroke marker is concerned, the cut-off value as defined above is preferably of at least the mean level of said at least one further stroke marker in biological samples obtained from an apparently healthy population of individuals.

It is well within the ordinary skills of one of skill in the art to determine cut-off values according to the invention. In particular, care should preferably taken to measure the level of proBNP(1-108), of fragments of proBNP(1-108) according to the invention, or of the at least one further stroke marker, in biological samples which are of the same nature. As intended herein, "an apparently healthy population of individuals" relates to individuals which preferably present none of the symptoms indicative of stroke as defined above.

Where the level of proBNP(1-108), or of fragments of proBNP(1-108), and the level of the at least one further stroke marker, are compared with one or several cut-off values, this means that the level of proBNP(1-108), or of fragments of proBNP(1-108), on one hand, and the level of the at least one further stroke marker, on the other hand, can be each compared to respective cut-off values, or that they can be both compared to a single cut-off value.

It is preferred that the level of the at least further stroke marker or of the at least one marker of cardiovascular diseases is measured in the same biological sample as that in which the level of proBNP(1-108), or of fragments of proBNP(1-108), is measured.

As intended herein, the expression "biological sample" includes both the sample as taken and the sample which has been subjected to various treatments, in particular to render it suitable for use in the processes and methods according to the invention. The biological sample according to the invention can be of any type, however it is preferred that the biological sample is selected from the group constituted of a blood sample, a serum sample, a plasma sample, a cerebrospinal fluid sample, a urine sample and a saliva sample.

EXAMPLES

Example 1

1. Methods
a. Samples

The levels of proBNP(1-108) and H-FABP were determined in 70 serum samples obtained from individuals in whom a stroke has occurred less than 3 hours after onset (15 hemorrhagic stroke samples (HM) and 55 ischemic stroke samples (IM)) and in 148 control serum samples from apparently healthy individuals.

b. Biomarker measurement The proBNP(1-108) level was determined using the BioPlex™2200 proBNP(1-108) assay (Bio-Rad).

The BioPlex™2200 combines multiplex, magnetic bead and flow cytometry technologies to provide multi-analyte detection on a fully automated random access platform. Magnetic particles (8 μm diameter, carboxyl-modified surface) are dyed with 2 fluorophores (classification dyes, CL1 and CL2) which emit at distinct wavelengths and adsorb significantly at 635 nm. The reporter fluorophore, β-phycoerythrin (PE) was chosen for its high molar extinction coefficient, quantum yield, resistance to photobleaching, lack of self-quenching and stability. The detector simultaneously measures light at 3 wavelengths: the 2 classification dyes and the reporter dye.

The BioPlex™2200 proBNP(1-108) assay is a two-step sandwich fluorescence immunoassay. In a first step, the BioPlex™2200 system combines 50 μL of patient sample, magnetic dyed beads coated with the anti-proBNP(1-108) monoclonal antibody secreted by the hybridoma deposited at the CNCM under reference number I-3073 and assay buffer into a reaction vessel. Then, after 11 minutes of incubation and wash cycles, anti-human BNP monoclonal antibody secreted by the hybridoma deposited at the CNCM under reference number I-3746 conjugated to phycoerythrin (PE) is added and incubated for 2 minutes. After removal of excess conjugate, the bead mixture is passed through the detector which identifies the dyed beads and the amount of antigens captured on the beads by the fluorescence of PE. After calibration using a set of 6 distinct calibrators, the 3 levels of quality controls and patient samples results are expressed in pg/mL.

Two Quality Control beads are also tested with each sample to enhance the integrity of the overall system.

The H-FABP level was determined with the human H-FABP ELISA kit from Hycult biotechnology according to the manufacturer instructions.

c. Statistical Analysis

Distribution of biomarkers according to patient status was represented by boxplot representation, which is a convenient way of graphically depicting groups of numerical data through their five-number summaries (the smallest observation, lower quartile (Q1), median (Q2), upper quartile (Q3), and largest observation).

Data have been normalized using the Box-Cox method to follow a Gaussian distribution and enable statistical analysis (Box, G. E. P. and Cox, D. R. (1964) An analysis of transformations. JRSS B 26, 211-246).

Differential analysis between the control and stroke samples were done using the following statistical tests: the Wilcoxon Rank Sum Test (Wilcoxon, F. (1945). Individual comparisons by ranking methods. Biometrics, 1, 80-83) which is non-parametric (requires no assumption of statistical distribution and which can be an alternative to Student's t-test) and the Welch's test which is an adaptation of Student's t-test intended for use with two samples having possibly unequal variances. The analysis also includes the adjusted (corrected) versions of these tests by the Benjamini/Hochber method (Benjamini and Y. Hochberg (1995). Controlling the False Discovery Rate: a practical and powerful approach to multiple testing. J. R. Statist. Soc. B. Vol. 57: 289-300) was also performed.

The diagnostic performance of the markers was characterized by two indices: sensitivity (ability to detect the diseased population) and specificity (ability to detect the control population). The result of a diagnostic test can be further characterized by determining the area under the curve (AUC) of a ROC (receiver operating characteristic) analysis. The ROC curves are a graphical visualization of the reciprocal relation between the sensitivity (Se) and the specificity (Sp) of a test for various concentrations (M. H. Zweig and G. Campbell (1993). "Receiver-operating characteristic (ROC) plots: a fundamental evaluation tool in clinical medicine". Clinical chemistry 39 (8): 561-57).

2. Results
a) Distribution of Biomarkers by Boxplot Representation

Figure 1:
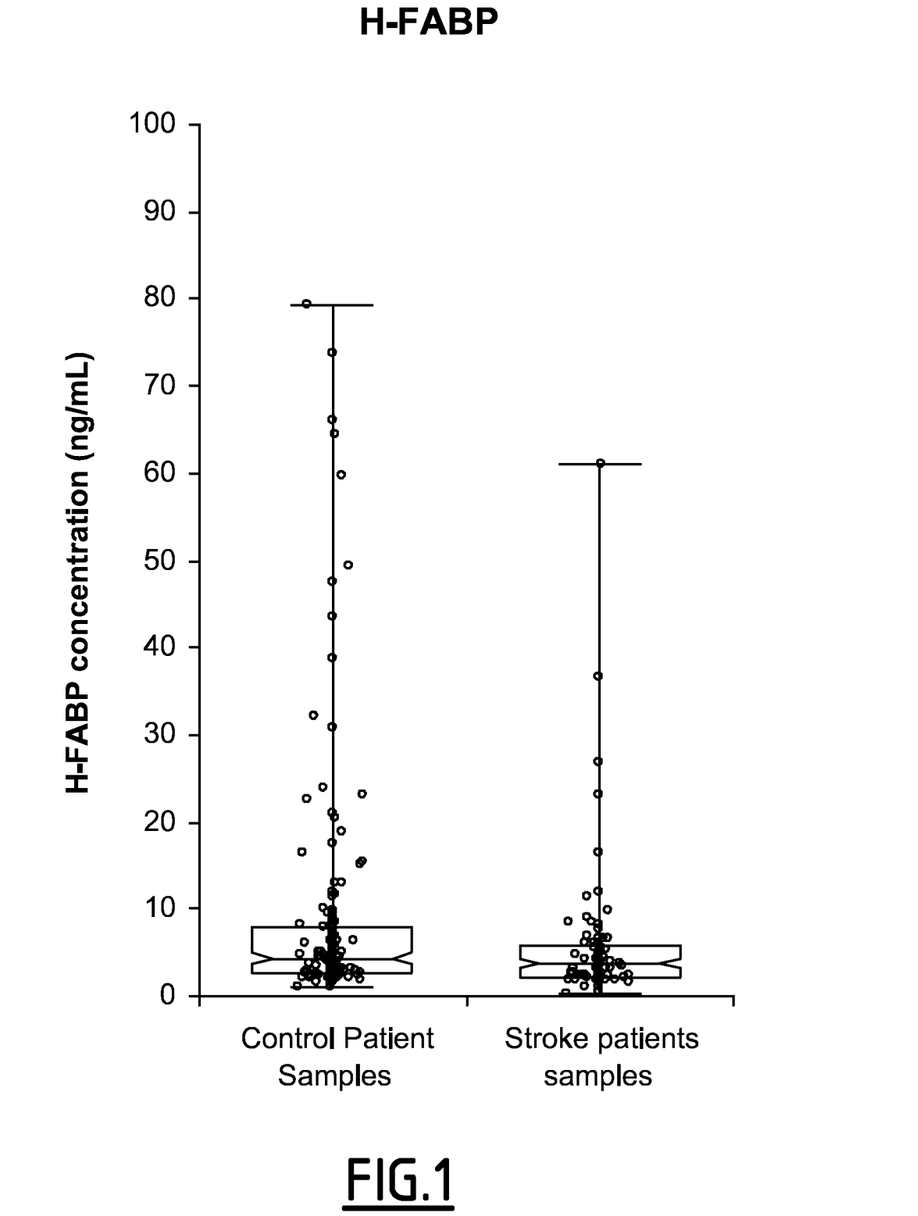
FIG. 1 represents the distribution of H-FABP concentrations (vertical axis, ng/ml) in Stroke and Control populations.
Figure 2:
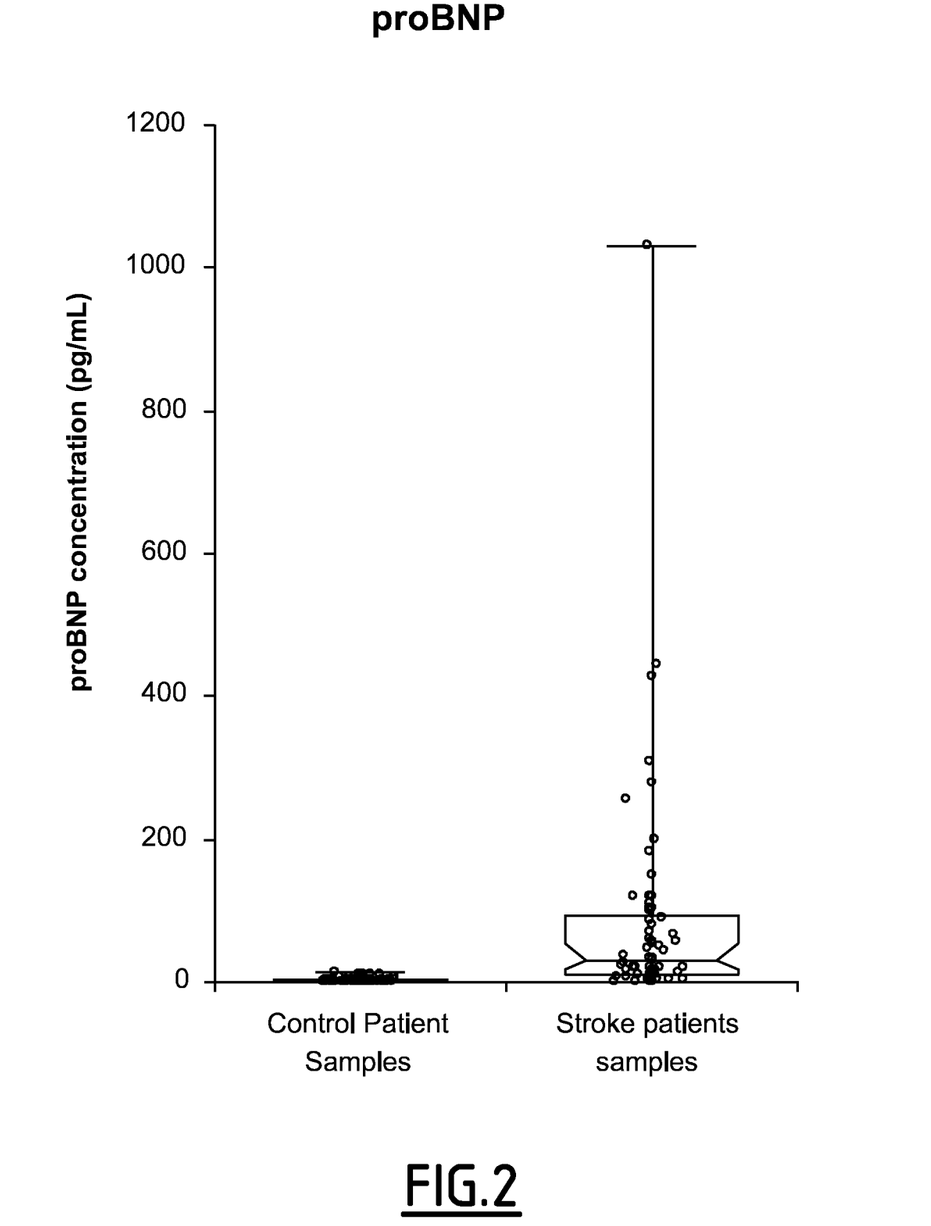
FIG. 2 represents the distribution of proBNP(1-108) concentrations (vertical axis, pg/ml) in Stroke and Control populations.

FIGS. 1 and 2 respectively represent the distribution of H-FABP and proBNP(1-108) concentrations in Stroke and Control populations.

TABLE 1

H-FABP and proBNP(1-108) levels in Control and Stroke populations:

| Markers | Populations | Min | 1st Quartile | Median | 95% CI | 3rd Quartile | Max | IQR |
|---|---|---|---|---|---|---|---|---|
| H-FABP | Control subjects | 1.0 | 2.78 | 4.27 | 3.59-5.10 | 7.95 | 79.4 | 5.17 |
|  | Stroke patients | 0.2 | 2.24 | 3.60 | 3.07-4.21 | 5.80 | 61.0 | 3.55 |
| proBNP | Control subjects | 0.0 | 0.40 | 1.20 | 0.90-1.50 | 2.00 | 12.9 | 1.60 |
|  | Stroke patients | 0.0 | 9.03 | 31.05 | 18.15-53.10 | 91.83 | 1032.0 | 82.80 |

ProBNP(1-108) marker shows higher concentration levels in stroke samples than in control samples. Whereas H-FABP concentrations measured show no significant difference between the stroke patient samples and the control samples.

b) Differential Analysis

The statistical significance of the difference in H-FABP and proBNP(1-108) levels between stroke samples and control samples was determined:

TABLE 2

Differential analysis between concentrations determined from the Control and the Stroke population for H-FABP and proBNP(1-108) markers

| Markers | pWILCOXbrut | pWILCOXadj | pWELCHbrut | pWELCHadj |
|---|---|---|---|---|
| H-FABP | 0.0131 | 0.016375 | 0.0006 | 0.001 |
| proBNP | 0.0001 | 0.000167 | 0.0001 | 0.00025 |

The difference in concentrations between the stroke samples and the control samples is statistically significant for both markers (proBNP(1-108) and H-FABP), however the proBNP(1-108) presents particularly interesting characteristics with very low p-values ($10^{-4}$) (Table 2).

c) ROC Curve Analysis

Based on Receiving-Operating-Characteristic (ROC) analysis for clinical status and as summarized in Table 3, the area under the curve for proBNP(1-108) succeed in discriminating patients diagnosed for stroke from healthy subjects, with a sensitivity of 90%, a specificity of 85%. Moreover, this discriminatory power is very high for both ischemic and hemorrhagic stroke patients with respective AUC of 0.936 and 0.935.

TABLE 3

Receiving-Operation-Characteristic analysis data for proBNP(1-108) for Stroke patients when compared to Control subjects

| proBNP | Sample sizes | Cut-off determined from normalized values | Se | Sp | AUC | IC 95% |
|---|---|---|---|---|---|---|
| Ctrl vs Stroke | (148) vs (70) | 1.189 | 90% | 85% | 0.935 | 0.883-0.965 |
| Ctrl vs IM | (148) vs (55) | 2.409 | 82% | 95% | 0.936 | 0.874-0.969 |
| Ctrl vs HM | (148) vs (15) | 2.579 | 80% | 96% | 0.935 | 0.793-0.982 |

As shown in table 4 below, the H-FABP marker has a low discriminatory power for the stroke diagnosis with a sensitivity of 57%, a specificity of 54.7%.

TABLE 4

Receiving-Operation-Characteristic analysis data for H-FABP for Stroke patients when compared to Control subjects

| H-FABP | Sample sizes | Cut-off determined from normalized values | Se | Sp | AUC | IC 95% |
|---|---|---|---|---|---|---|
| Ctrl vs Stroke | (148) vs (70) | -1.190 | 57% | 55% | 0.612 | 0.532-0.687 |
| Ctrl vs IM | (148) vs (55) | -1.00 | 58% | 55% | 0.618 | 0.533-0.696 |
| Ctrl vs HM | (148) vs (15) | -1.149 | 53% | 55% | 0.563 | 0.416-0.749 |

Example 2

1. Methods
a. Samples

The levels of proBNP(1-108) were determined in 23 serum samples obtained from individuals in whom a stroke has occurred less than 3 hours after onset (5 hemorrhagic stroke samples (HM) and 18 ischemic stroke samples (IM)), in 7 serum samples obtained from individuals in whom a TIA has been clinically diagnosed, and in 94 control serum samples from apparently healthy individuals.

b. Marker Level Determination

The proBNP(1-108) level was determined as indicated in Example 1.

c. Statistical Analysis

Boxplot representation of proBNP(1-108) levels distribution, and ROC analysis were conducted as indicated in Example 1.

2. Results a) Distribution of Biomarkers by Boxplot Representation

Figure 3:
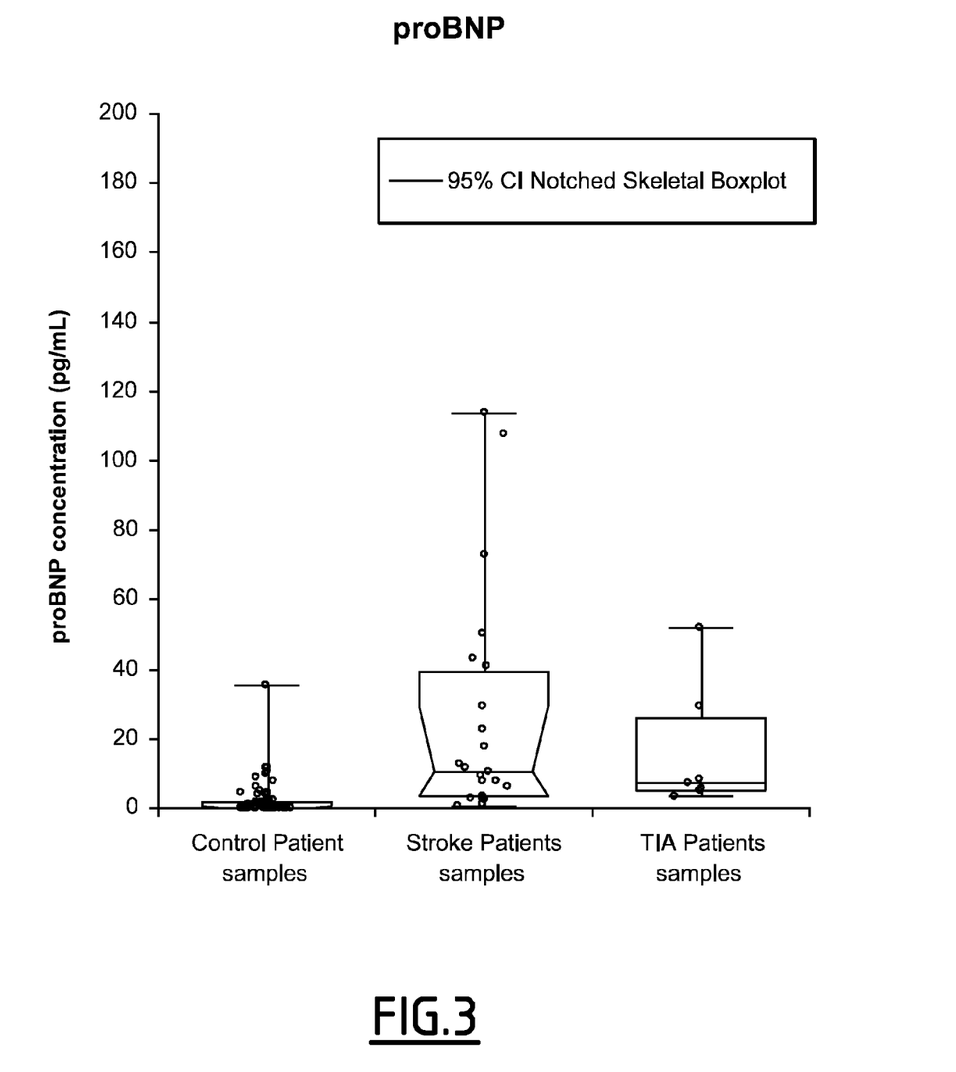
FIG. 3 represents the distribution of proBNP(1-108) concentrations (vertical axis, pg/ml) in Stroke, TIA and Control populations.

FIG. 3 represents the distribution of proBNP(1-108) concentrations in Stroke, TIA and Control populations.

TABLE 5 proBNP(1-108) distribution values in Control, TIA and Stroke populations

|  | Min | 1st Quartile | Median | 95% CI | 3rd Quartile | Max | IQR |
|---|---|---|---|---|---|---|---|
| Control Subjects samples | 0 | 0.0 | 0.2 | 0.0-0.8 | 1.7 | 35 | 1.7 |
| Stroke Patients samples | 1 | 3.1 | 10.3 | 3.3-29.5 | 39.0 | 114 | 35.9 |
| TIA Patients samples | 3 | 5.1 | 7.2 | 3.4-51.7 | 25.8 | 52 | 20.7 |

ProBNP(1-108) marker shows higher concentration levels in stroke or TIA patient samples than in control samples.

b) ROC Curve Analysis

Based on Receiving-Operating-Characteristic (ROC) analysis for clinical status and as summarized in Table 6, the area under the curve for proBNP(1-108) succeed in discriminating patients diagnosed for stroke from healthy subjects, with a sensitivity of 91%, a specificity of 84%.

TABLE 6

Receiving-Operation-Characteristic analysis data for proBNP(1-108) for Stroke patients when compared to Control patients

| proBNP | Sample sizes | Cut-off determined from raw values | Se | Sp | AUC | IC 95% |
|---|---|---|---|---|---|---|
| Ctrl vs Stroke | (94) vs (23) | 2.43 pg/mL | 91% | 84% | 0.913 | 0.720-0.989 | proBNP(1-108) power for diagnosing stroke patients evidenced in Example 1 are thus confirmed on these new pathological and healthy populations.

Example 3

The discriminatory power of proBNP(1-108) was further compared to that of two reference stroke markers of the prior art (S-100b and NSE) on identical populations.

1. Methods a. Samples

The levels of markers were determined in 41 plasma samples obtained from individuals in whom a stroke has occurred less than 3 hours after onset and in 51 control plasma samples from apparently healthy individuals.

b. Marker Level Determination

The proBNP(1-108) level was determined as indicated in Example 1.

The NSE level was determined using the Nexus DX™ Neuron Specific Enolase (NSE) Test kit from Nanogen according to the manufacturer instructions.

The S-100b level was determined using the Nexus DX™ S-100 ELISA Test kit from Nanogen according to the manufacturer instructions.

c. Statistical Analysis

The statistical analysis was conducted as indicated in Example 1.

2. Results a) Distribution of Biomarkers by Boxplot Representation

Figure 4:
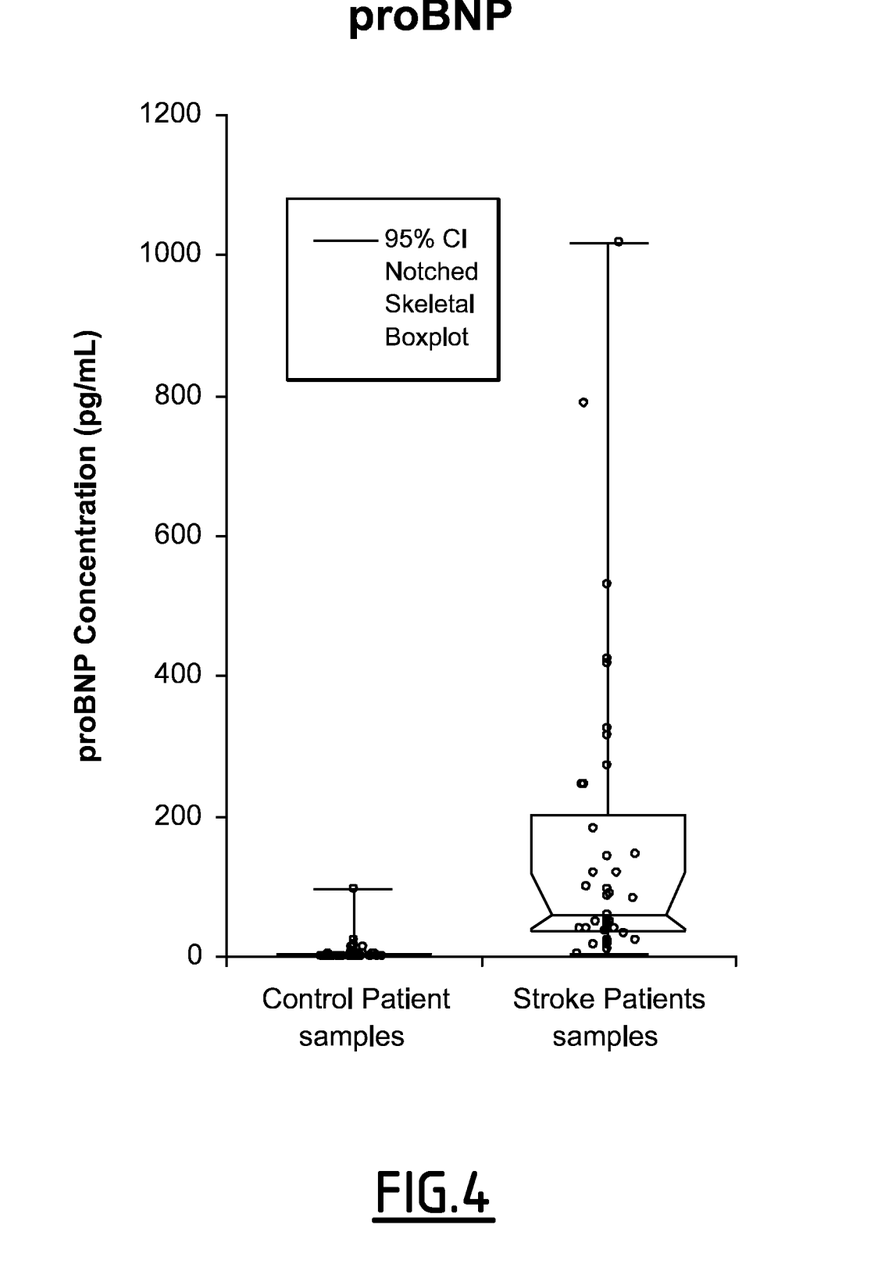
FIG. 4 represents the distribution of proBNP(1-108) concentrations (vertical axis, pg/ml) in Stroke and Control populations.
Figure 5:
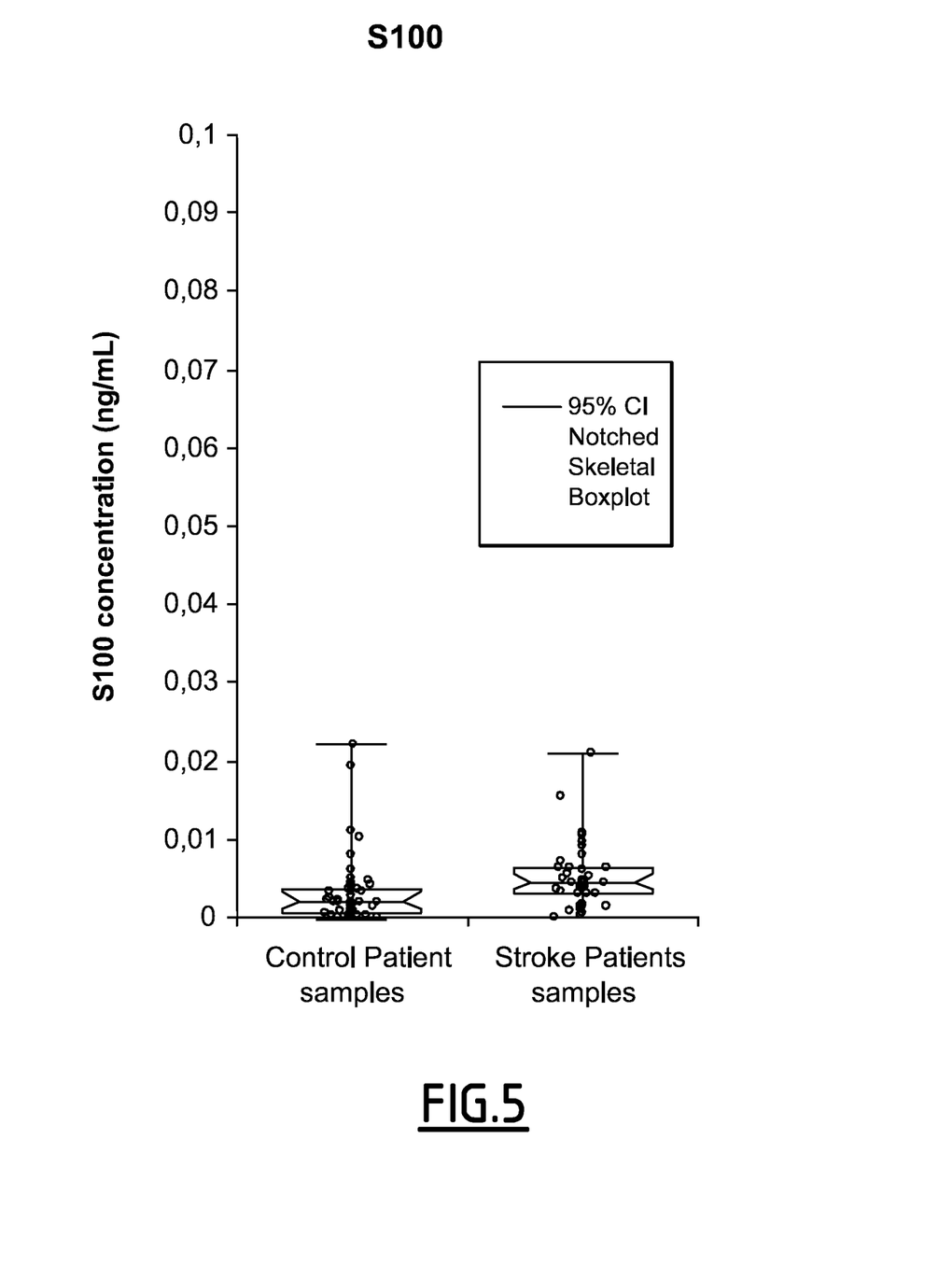
FIG. 5 represents the distribution of S-100b concentrations (vertical axis, ng/ml) in Stroke and Control populations.
Figure 6:
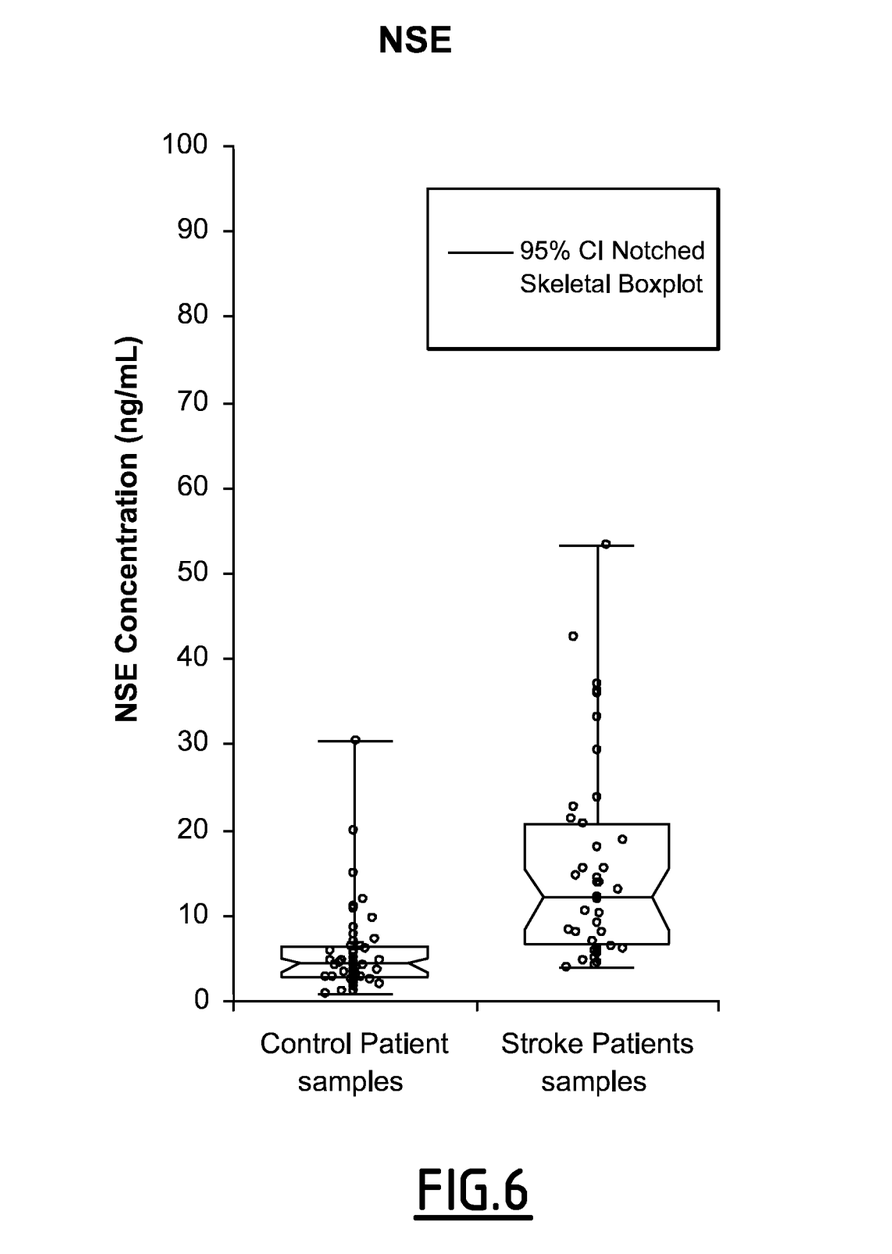
FIG. 6 represents the distribution of NSE concentrations (vertical axis, ng/ml) in Stroke and Control populations.

FIGS. 4, 5 and 6 respectively represent the distribution of proBNP(1-108), S-100b and NSE concentrations in Stroke and Control populations.

TABLE 7 proBNP(1-108), S100 and NSE distribution values in Control and Stroke populations

| Markers | Populations | Min | 1st Quartile | Median | 95% CI | 3rd Quartile | Max | IQR |
|---|---|---|---|---|---|---|---|---|
| proBNP | Control Subjects | 0 | 0.3 | 1.4 | 0.7 to 1.,9 | 2.5 | 97 | 2.3 |
| | Stroke Patients | 2 | 35.3 | 59.6 | 40.4 to 120.6 | 203.7 | 1019 | 168.3 |
| S100 | Control Subjects | 0.00 | 0.000 | 0.002 | 0.001 to 0.003 | 0.003 | 0.02 | 0.003 |
| | Stroke Patients | 0.00 | 0.003 | 0.004 | 0.004 to 0.006 | 0.006 | 0.02 | 0.003 |
| NSE | Control Subjects | 0.88 | 2.846 | 4.414 | 3.413 to 4.988 | 6.229 | 30.33 | 3.383 |
| | Stroke Patients | 3.87 | 6.766 | 12.085 | 8.165 to 15.607 | 20.843 | 53.26 | 14.077 |

ProBNP(1-108) and NSE markers show higher concentration levels in stroke samples than in control samples. The best discrimination between both populations is observed with the proBNP(1-108) marker. Whereas S-100 concentrations measured show no significant difference between the stroke patient samples and the control samples.

b) Differential Analysis

The statistical significance of the difference in proBNP(1-108), NSE and S-100 levels in stroke samples and in control sample was determined:

TABLE 8

Differential analysis between concentrations determined from the Control and the Stroke populations for NSE, S-100 and proBNP(1-108) markers

| Markers | pWILCOXbrut | pWILCOXadj | pWELCHbrut | pWELCHadj |
|---|---|---|---|---|
| NSE | 0.0001 | 0.0003 | 0.0001 | 0.0003 |
| S-100 | 0.0023 | 0.0037 | 0.0064 | 0.0102 |
| proBNP | 0.0001 | 0.0003 | 0.0001 | 0.0003 |

NSE and proBNP(1-108) are statistically significant with very low p values ($p<0.001$), c) ROC Curve Analysis Based on Receiving-Operating-Characteristic (ROC) analysis for clinical status and as summarized in Table 9, the area under the curve for proBNP(1-108) succeed in discriminating patients diagnosed for stroke from healthy subjects, with a sensitivity of 95%, a specificity of 95% and an AUC of 0.974.

TABLE 9

Receiving-Operation-Characteristic analysis data for proBNP(1-108), NSE and S100 for Stroke patients when compared to Control subjects

| Ctrl vs Stroke | Sample sizes | Cut-off | Se | Sp | AUC | IC 95% |
|---|---|---|---|---|---|---|
| proBNP (1-108) | (55) vs (41) | 3.26 | 95% | 95% | 0.974 | 0.904-0.993 |
| NSE | (55) vs (41) | 1.682 | 85% | 73% | 0.857 | 0.770-0.915 |
| S-100b | (55) vs (41) | -6.644 | 39% | 89% | 0.636 | 0.504-0.751 |

It can be seen that proBNP(1-108) presents a high discriminatory power over that offered by NSE and S-100b to discriminate the Stroke patient from the Control subjects.

Example 4

The diagnostic power of proBNP(1-108) was further assessed in patients with ischemic stroke using the BioPlex™2200 proBNP(1-108) assay as described in Example 1.

a) Samples 32 citrated plasma samples from patients with ischemic stroke admitted to the Emergency Department within 3 hours of the Stroke onset were tested. The stroke severity was assessed by the National Institutes of Health Stroke Scale (NIHSS).

42 citrated plasma samples from apparently healthy blood donor matched by gender and age with the patients from the Stroke population were tested.

All the citrated plasma samples were stored at −80° C. Prior the analysis, the samples were thawed and centrifuged at 3000 g for 15 min at 4° C.

b) Results

The distributions of the proBNP(1-108) values for the Control and the ischemic stroke populations are shown in Table 10. The level of proBNP(1-108) was significantly higher in the ischemic stroke group compared to the control group (Mann-Whitney, $p<0.0001$). The results confirm that the proBNP(1-108) is thus a useful plasma biomarker for the early diagnosis of Ischemic stroke.

TABLE 10 proBNP(1-108) concentrations in ischemic stroke and control citrated plasma samples (minimum, $1^{st}$ quartile, median, $3^{rd}$ quartile and maximum values)

| Populations | Minimum (pg/mL) | $1^{st}$ Quartile (pg/mL) | Median (pg/mL) | $3^{rd}$ Quartile (pg/mL) | Maximum (pg/mL) |
|---|---|---|---|---|---|
| Control population (N = 42) | 0 | 0 | 1 (IC95%: 0-2) | 2 | 23 |
| Ischemic Stroke population (N = 32) | 2 | 34 | 71 (IC95%: 38-145) | 219 | 1019 |

The invention claimed is:

1. A method for the in vitro diagnosis of stroke and transient ischemic attack (TIA) in an individual, comprising the following steps:
 (a) measuring the level of proBNP(1108), or of fragments of proBNP(1-108) comprising a RAPRSP sequence (SEQ ID NO: 1), in a biological sample of the individual;
 (b) comparing the measured level with a cut-off value;
 (c) determining therefrom whether a stroke or a TIA has occurred in the individual,
 wherein a measured level higher than the cut-off value is indicative of a stroke or a TIA;
 wherein the level of proBNP(1-108), or of fragments of proBNP(1-108), is determined using an immunoassay which comprises an antibody targeting an epitope which comprises the RAPRSP sequence (SEQ ID NO: 1).

2. The method according to claim 1, wherein the fragments of proBNP(1-108) further comprise a FGRKMDR sequence (SEQ ID NO: 2).

3. The method according to claim 1, wherein the fragments of proBNP(1-108) comprise the sequence of BNP (77-108) (SEQ ID NO: 3).

4. The method according to any of claim 1, wherein the stroke is selected from the group consisting of an ischemic stroke, a hemorrhagic stroke, and a transient ischemic attack (TIA).

5. The method according to any of claim 1, wherein step (a) is implemented within 6 hours after the onset of at least one symptom indicative of stroke in the individual.

6. The method according to claim 1, wherein the antibody targeting an epitope which comprises the RAPRSP sequence (SEQ ID NO: 1) is secreted by the hybridoma deposited at the CNCM (Paris, France) under the Budapest Treaty on Apr. 29, 2005, under reference number I3073.

7. The method according to claim 6, wherein the immunoassay further comprises an antibody targeting an epitope which comprises the FGRKMDR sequence (SEQ ID NO: 2).

8. The method according to claim 1, wherein the cut-off value is of at least 1 pg/ml.

9. The method according to claim 1, comprising the following steps:
 (a') measuring the level of proBNP(1-108), or of fragments of proBNP(1-108) comprising a RAPRSP sequence (SEQ ID NO: 1), in a biological sample of the individual;
 (b') measuring the level of at least one further stroke marker in a biological sample of the individual;
 (c') comparing the level of proBNP(1-108), or of fragments of proBNP(1-108), and the level of the at least one further stroke marker, with one or several cut-off values;
 (d') determining therefrom whether a stroke or a TIA has occurred in the individual;
 wherein the level of proBNP(1-108), or of fragments of proBNP(1-108), is determined using an immunoassay which comprises an antibody targeting an epitope which comprises the RAPRSP sequence (SEQ ID NO: 1).

10. The method according to claim 9, wherein the level of the at least further stroke marker is measured in the same biological sample as that in which the level of proBNP(1-108), or of fragments of proBNP(1-108), is measured.

11. The method according to claim 1, wherein the biological sample is selected from the group constituted of a blood sample, a serum sample, a plasma sample, a cerebrospinal fluid sample, a urine sample and a saliva sample.

12. The method according to claim 1, further comprising measuring the level of at least one marker of cardiovascular diseases.

13. The method according to claim 12, wherein the at least one marker of cardiovascular diseases is selected from the group consisting of CRP and cTnI.

14. The method according to claim 7, wherein the immunoassay is a sandwich immunoassay and wherein the antibody targeting an epitope which comprises the RAPRSP sequence (SEQ ID NO: 1) is a capture antibody and the antibody targeting an epitope which comprises the FGRKMDR sequence (SEQ ID NO: 2) is a detection antibody.

15. The method according to claim 14, wherein the cut-off value is of at least 1 pg/ml.

16. The method according to claim 7, wherein the antibody targeting an epitope which comprises the FGRKMDR sequence (SEQ ID NO: 2) is secreted by the hybridoma deposited at the CNCM (Paris, France) under the Budapest Treaty on Apr. 13, 2007, under reference number I-3746.

17. The method according to claim 16, wherein the immunoassay further comprises an antibody targeting an epitope which comprises the FGRKMDR sequence (SEQ ID NO: 2).

18. The method according to claim 17, wherein the antibody targeting an epitope which comprises the FGRKMDR sequence (SEQ ID NO: 2) is secreted by the hybridoma deposited at the CNCM (Paris, France) under the Budapest Treaty on Apr. 13, 2007, under reference number I-3746.

19. The method according to claim 18, wherein the immunoassay is a sandwich immunoassay and wherein the antibody secreted by the hybridoma deposited at the CNCM (Paris, France) under the Budapest Treaty on Apr. 29, 2005, under reference number I-3073 is a capture antibody, and the antibody secreted by the hybridoma deposited at the CNCM (Paris, France) under the Budapest Treaty on Apr. 13, 2007, under reference number I-3746 is a detection antibody.

20. A method for the in vitro diagnosis of stroke and transient ischemic attack (TIA) in an individual, comprising the following steps:
 (a) measuring the level of proBNP(1-108), or of fragments of proBNP(1-108) comprising a RAPRSP sequence (SEQ ID NO: 1), in a biological sample of the individual;
 (b) comparing the measured level with a cut-off value;
 (c) determining therefrom whether a stroke or a TIA has occurred in the individual, wherein a measured level higher than the cut-off value is indicative of a stroke or a TIA; and wherein the level of proBNP(1-108), or of fragments of proBNP(1-108), i determined using an immunoassay which comprises an antibody targeting an epitope which comprises the RAPRSP sequence (SEQ ID NO: 1), wherein the antibody targeting an epitope which comprises the RAPRSP sequence (SEQ ID NO: 1) is secreted by the hybridoma deposited at the CNCM (Paris, France) under the Budapest Treaty on Apr. 29, 2005, under reference number I-3073.

21. A method for treating at least one of stroke and transient ischemic attack (TIA) in an individual having a level of proBNP(1-108) or of fragments of proBNP(1-108) comprising a RAPRSP sequence (SEQ ID NO: 1) in a biological sample higher than a cut-off value, comprising the following steps:

(a) measuring the level of proBNP(1-108), or of fragments of proBNP(1-108) comprising a RAPRSP sequence (SEQ ID NO: 1), in a biological sample of the individual;

(b) comparing the measured level with a cut-off value; and (c) if the measured level is higher than the cut-off value, administrating to said individual a therapeutically efficient amount of clot-dissolving agents.

* * * * *

SEQUENCE LISTING

<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Arg Ala Pro Arg Ser Pro
1               5

<210> SEQ ID NO 2
<211> LENGTH: 7
<212> TYPE: PRT
<213> ORGANISM: Homo sapiens

<400> SEQUENCE: 2

Phe Gly Arg Lys Met Asp Arg
1               5

<210> SEQ ID NO 3
<211> LENGTH: 32
<212> TYPE: PRT
<213> ORGANISM: Homo sapiens

<400> SEQUENCE: 3

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

<210> SEQ ID NO 4
<211> LENGTH: 108
<212> TYPE: PRT
<213> ORGANISM: Homo sapiens

<400> SEQUENCE: 4

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

-continued

```
Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105
```